(12) United States Patent
Deng

(10) Patent No.: US 11,267,775 B2
(45) Date of Patent: Mar. 8, 2022

(54) METHOD FOR PREPARING CANNABIDIOL BY SEPARATION AND PURIFICATION USING HIGH-SPEED COUNTERCURRENT CHROMATOGRAPHY

(71) Applicant: Techson Industry Company Limited, Hong Kong (HK)

(72) Inventor: Qiuyun Deng, Hong Kong (CN)

(73) Assignee: Techson Industry Company Limited, Hong Kong (HK)

( * ) Notice: Subject to any disclaimer, the term of this patent is extended or adjusted under 35 U.S.C. 154(b) by 0 days.

(21) Appl. No.: 17/311,991

(22) PCT Filed: Apr. 19, 2019

(86) PCT No.: PCT/CN2019/083401
§ 371 (c)(1),
(2) Date: Jun. 8, 2021

(87) PCT Pub. No.: WO2020/119001
PCT Pub. Date: Jun. 18, 2020

(65) Prior Publication Data
US 2022/0009867 A1 Jan. 13, 2022

(30) Foreign Application Priority Data
Dec. 14, 2018 (CN) .......................... 201811534794.4

(51) Int. Cl.
| *C07C 37/72* | (2006.01) |
| *C07C 37/82* | (2006.01) |
| *B01D 15/00* | (2006.01) |
| *B01D 15/42* | (2006.01) |
| *B01D 15/18* | (2006.01) |

(52) U.S. Cl.
CPC .......... *C07C 37/72* (2013.01); *B01D 15/1807* (2013.01); *B01D 15/426* (2013.01); *C07C 37/82* (2013.01)

(58) Field of Classification Search
CPC ...... C07C 37/72; C07C 37/82; B01D 15/1807
See application file for complete search history.

(56) References Cited

U.S. PATENT DOCUMENTS 6,403,126 B1 6/2002 Webster et al.
2018/0362429 A1* 12/2018 Zhang ................... C07C 37/685

FOREIGN PATENT DOCUMENTS

| CN | 1621832 | 6/2005 |
| CN | 103739585 | 4/2014 |
| CN | 105505565 | 4/2016 |
| CN | 109942380 | 6/2019 |
| WO | 2004026802 | 4/2004 |
| WO | 2018032727 | 2/2018 |

OTHER PUBLICATIONS

"International Search Report (Form PCT/ISA/210) of PCT/CN2019/083401," dated Sep. 12, 2019, with English translation thereof, pp. 1-5.
Xiao Pei, Yun et al.,"Study on Hemp. III. Methods for Determination of Tetrahydrocannabinol and Cannabidiol in Different Growing Period of Hemp", Chinese Journal of Pharmaceuticals, vol. 39, Apr. 2008, with English abstract, pp. 281-284.

* cited by examiner

*Primary Examiner* — Sikarl A Witherspoon
(74) *Attorney, Agent, or Firm* — JCIP Global Inc.

(57) ABSTRACT

The present invention relates to a method for preparing cannabidiol by separation and purification using high-speed countercurrent chromatography, comprising: alcohol extraction and water precipitation, adsorption with a macroporous resin, and high-speed countercurrent chromatography separation. The present invention separates and obtains high-purity cannabidiol from industrial hemp flowers or leaves, while at the same time removing the psychotoxic component tetrahydrocannabinol by combining a macroporous resin chromatographic column with a high-speed countercurrent chromatograph, and optimizing process parameters, and the solvent used therein being environmentally friendly, leaving no residues, having low cost and being recyclable. Therefore, the method is suitable for industrial production.

9 Claims, 2 Drawing Sheets

METHOD FOR PREPARING CANNABIDIOL BY SEPARATION AND PURIFICATION USING HIGH-SPEED COUNTERCURRENT CHROMATOGRAPHY

CROSS-REFERENCE TO RELATED APPLICATION

This application is a 371 of international application of PCT application serial no. PCT/CN2019/083401, filed on Apr. 19, 2019, which claims the priority benefit of China application no. 201811534794.4, filed on Dec. 14, 2018. The entirety of each of the above mentioned patent applications is hereby incorporated by reference herein and made a part of this specification.

BACKGROUND

Technical Field

The present invention belongs to the field of cannabidiol extraction, and in particular relates to a method for preparing cannabidiol by separation and purification using high-speed countercurrent chromatography.

Description of Related Art

Cannabis (scientific name: *Cannabis sativa L.*) is an annual herbaceous plant in the family Cannabaceae and the genus *Cannabis*. Also known as hemp, Chinese hemp, fire hemp, mountain silk seedling and jute, it has significant agricultural and medicinal value. Up to now, people have isolated more than 500 types of substances from cannabis plants. Among them, cannabinol compounds have at least 86 types, and mainly include tetrahydrocannabinol (THC), cannabidiol (CBD), cannabinol (CBN) and cannabichromene (CBC), in which the first three account for 90% of cannabidiol compounds, and THC has been banned for a long time as it can cause hallucination and addiction to people, and can be used as a drug.

Given the high economic and medicinal value of hemp, the raw hemp used exclusively for industrial use is referred to as "industrial hemp". During its growth period, the hemp flowers or leaves have less than 0.3% tetrahydrocannabinol (THC), which make them unworthy for extraction of the toxic component tetrahydrocannabinol or direct ingestion as a drug. Thus, the hemp can be legally planted in a large scale, and for industrial development and utilization.

In recent years, it has been found by studies on the active ingredients of hemp that cannabidiol is not neurotoxic, and is a non-addictive active ingredient with obvious medicinal value. Moreover, pharmacological studies have shown that it can antagonize the effects of tetrahydrocannabinol on the human nervous system, and has pharmacological activities such as anti-spasm, sedative and hypnotic, anti-rheumatoid arthritis, and anti-anxiety effects. Hence, it is a natural active ingredient with very broad application prospects in the field of food and medicine.

Xiao Peiyun et al. published in "*Chinese Journal of Pharmaceuticals*" (Vol. 39, No. 4, 2008) a study on the comparison of methods of determining the contents of THC and CBD in industrial hemp during different growth periods. In this study, it was stated that during the fast-growth period, early flowering period, and full-bloom period, the content of THC was less than 0.3%, meeting the standard of industrial hemp, meanwhile the amount of CBD was also less than 0.3%, indicating that the CBD content was also very low in industrial hemp. Therefore, how to remove hallucinogenic and addictive ingredients such as THC as much as possible while ensuring productivity of high-purity CBD is a prerequisite for the CBD development and application.

At present, there are some reports in the public information about the methods of extracting cannabidiol from industrial hemp, most of which employ various column chromatography techniques, for example, the use of macroporous adsorption resin, MCI resin or octadecyl-bonded silica gel. Through comparative study, the methods of extracting cannabidiol from industrial hemp as mentioned in the prior art mainly have the following deficiencies:

1) The cannabinoids in industrial hemp plants comprise very complex components which are of more than 80 known types with similar polarities. Using the conventional methods for extraction and refinement often leads to low purity of CBD in the final product.

2) After extraction and purification, the psychotoxic component THC can still be detected, which means product safety is not guaranteed, product circulation is restricted, and industrial production and application are affected.

3) Separation and purification using repetitive column chromatography in the conventional technology would inevitably impair CBD, decrease productivity, and limit production capacity.

SUMMARY

The technical problem to be solved by the present invention is to provide a method for preparing cannabidiol by separation and purification using high-speed countercurrent chromatography. This method achieves better effects in removing impurities and tetrahydrocannabinol by combining a macroporous resin chromatographic column with a high-speed countercurrent chromatograph.

The present invention provides a method for preparing cannabidiol by separation and purification using high-speed countercurrent chromatography, comprising:

(1) subjecting industrial hemp flowers or leaves as raw materials to alcohol extraction and concentration, water precipitation, and vacuum rotary evaporation to obtain a crude hemp extract;

(2) dissolving the crude hemp extract in ethanol (diluted), then injecting it into a macroporous resin, followed by gradient elution to collect an elution section rich in cannabidiol, and performing vacuum rotary evaporation to obtain a crude extract of cannabidiol;

(3) performing separation and purification using high-speed countercurrent chromatography with n-hexane-ethyl acetate-methanol-water (or a tri-solvent system composed of n-hexane-methanol-water) as a separation solvent system to collect cannabidiol fractions, recover the solvent, followed by post-treatment to obtain cannabidiol.

The alcohol extraction and concentration in step (1) employs an ethanol solution with a concentration of 50~90% by volume, and the mass-volume ratio of the industrial hemp flowers or leaves to the ethanol solution is 1 g: (5~10) mL.

The water precipitation in step (1) is performed at a temperature of 5-8° C. for 24 h.

The macroporous resin in step (2) is D101 macroporous resin, AB-8 macroporous resin or HPD-100 macroporous resin.

The gradient elution in step (2) employs an ethanol solution with a concentration of 5~85% by volume; and the elution section of the ethanol solution with a concentration of 70~85% by volume is collected.

The n-hexane-ethyl acetate-methanol-water in step (3) has a volume ratio of 5:(0~1):5:(1~3).

The separation and purification using high-speed countercurrent chromatography in step (3) specifically comprises: taking one phase in the separation solvent system as a stationary phase and another phase as a mobile phase; pumping the stationary phase at a flow rate of 30~50 mL/min into a high-speed countercurrent chromatograph, and pumping the mobile phase at a flow rate of 5-10 mL/min under the condition of 25~35° C. and a rotational speed of the main engine being 700~4000 r/min; after the two phases reach equilibrium, dissolving the crude extract of cannabidiol with the mobile phase, followed by collecting cannabidiol fractions after detecting by a detector.

Among them, the upper phase in the solvent system serves as the stationary phase, and the lower phase serves as the mobile phase; or the lower phase in the solvent system serves as the mobile phase, and the upper phase serves as the mobile phase. The high-speed countercurrent chromatograph can adopt the forward-connection and forward-rotation mode or the forward-connection and backward-rotation mode. The forward connection refers to the mode of connection from the head end to the tail end.

The crude extract of cannabidiol after being dissolved with the mobile phase has a concentration of 50~100 mg/mL and an injection volume is 20 mL; and the detection wavelength is 220 nm.

The post-treatment in step (3) includes concentration under reduced pressure, crystallization, and vacuum freeze-drying.

After the sample of the present invention is subjected to crude separation by the macroporous adsorption resin, most of the impurities are removed, and cannabidiol is concentrated; the sample is then subjected to fine separation by the high-speed countercurrent chromatograph to further remove impurities, especially to remove tetrahydrocannabinol, and reduce loss so that cannabidiol can be produced in a large scale.

Compared with column chromatography and other methods, the high-speed countercurrent chromatography of the present invention does not use any solid carrier. As such, there would be no irreversible adsorption and loss of the sample caused by solid carriers, and the separation effect would be high; the raw materials can be utilized to the greatest extent, and the production cost is reduced. In addition, the entire separation process is carried out in a closed device, and the preparation process is simple and convenient, safe, environmental friendly, and sustainable. Therefore, it is an efficient and quick method for separating high-purity CBD from industrial hemp.

Beneficial Effects

By combining a macroporous resin chromatographic column with a high-speed countercurrent chromatograph, and optimizing process parameters, the present invention separates and obtains high-purity cannabidiol from industrial hemp flowers or leaves, while at the same time removing the psychotoxic component tetrahydrocannabinol, and the solvent used therein being environmentally friendly, leaving no residues, having low cost and being recyclable. Therefore, it is suitable for industrial production.

DESCRIPTION OF THE EMBODIMENTS

The present invention will be further explained below in conjunction with specific Examples. It should be understood that these Examples are only used to illustrate the present invention rather than limit the scope of the present invention. In addition, it should also be understood that after reviewing the disclosure of the present invention, a person skilled in the art can make various changes or modifications to the present invention, and these equivalent forms also fall within the scope defined by the appended claims of the present application.

EXAMPLE 1

(1) 10 kg industrial hemp was ground and dried, and added into a 70% aqueous ethanol solution at the material to liquid ratio of 1:5 (w/v, g/mL) to be mixed thoroughly and ultrasonically extracted for 120 min (control the temperature to below 45° C., and keep away from light). After ultrasonication, vacuum filtration was carried out, and the resulting filter residue was extracted repetitively for twice under the same conditions. The filtrate was combined, with the ethanol removed by vacuum rotary evaporation at 45° C., and then concentrated to have a relative density of 1.2, and 5-7 times of purified water was added. Under the condition of 5-8° C., it was subjected to water precipitation for 24 h, and filtered. The precipitate was dried under reduced pressure to obtain a crude hemp extract.

Figure 1:
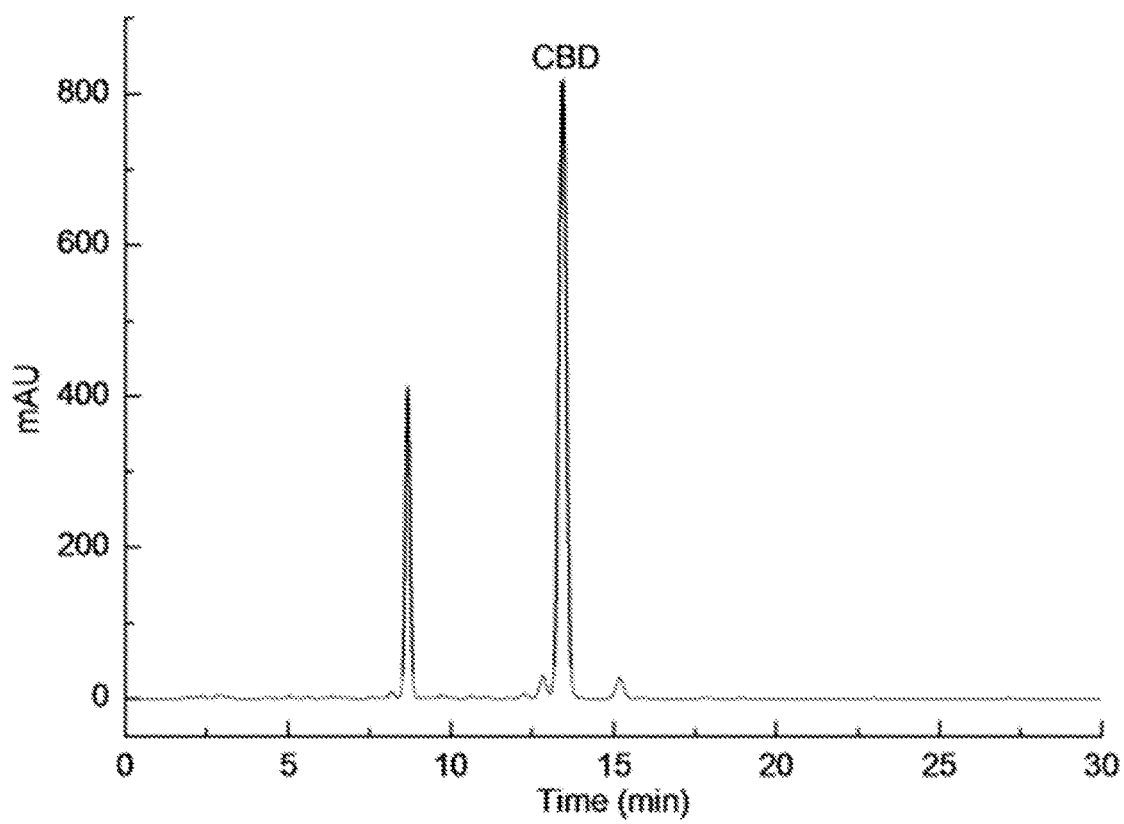
FIG. 1 is a high performance liquid chromatogram of the crude extract of cannabidiol in Example 1.

(2) The AB-8 macroporous resin was soaked in ethanol for 24 h, and then loaded into the chromatography column. It was washed with ethanol until the eluent in combination with the same volume of deionized water became a transparent solution. Then, it was washed with deionized water until the effluent was neutral; the crude hemp extract was dissolved in ethanol, and then injected into the AB-8 macroporous resin until the adsorption volume reached ⅔ of the total volume of the resin. The resin was first rinsed with deionized water at a flow rate of 2 BV/h, then rinsed with 10%, 30%, 50% and 70% aqueous ethanol solution respectively at a flow rate of 2 BV/h, and 70% elution fractions were collected. The ethanol was removed by vacuum rotary evaporation at 45° C. to obtain a crude extract of cannabidiol. The high performance liquid chromatogram is as illustrated in FIG. 1.

Figure 2:
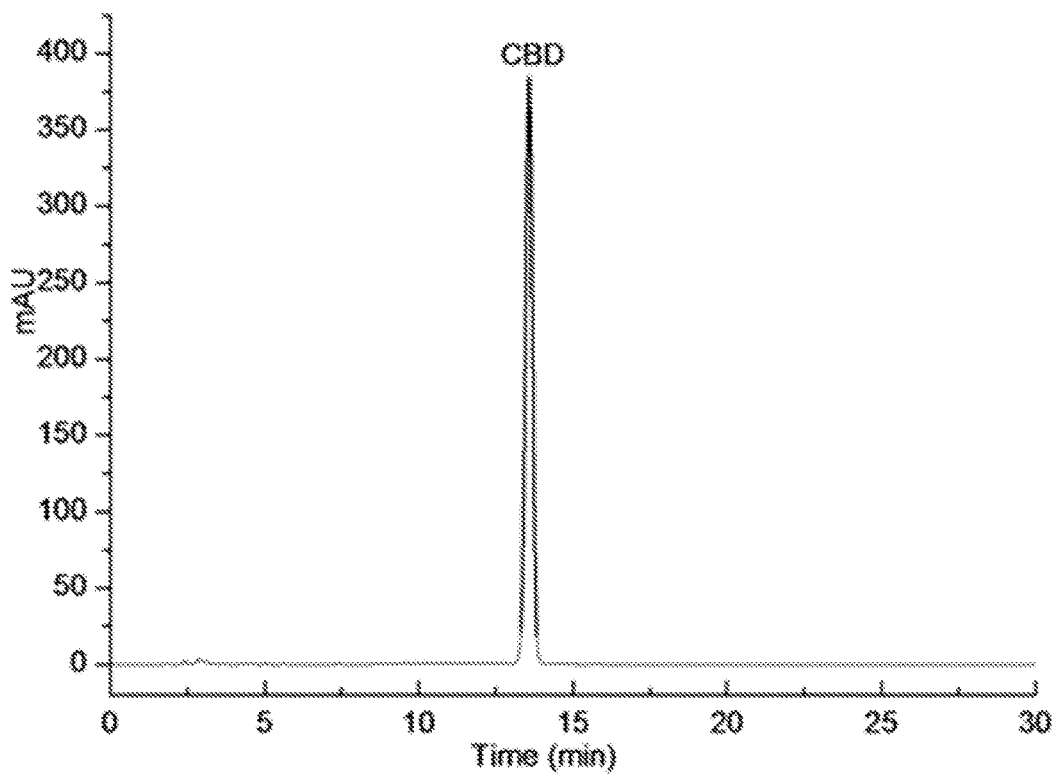
FIG. 2 is a high performance liquid chromatogram of the final product cannabidiol in Example 1.
Figure 3:
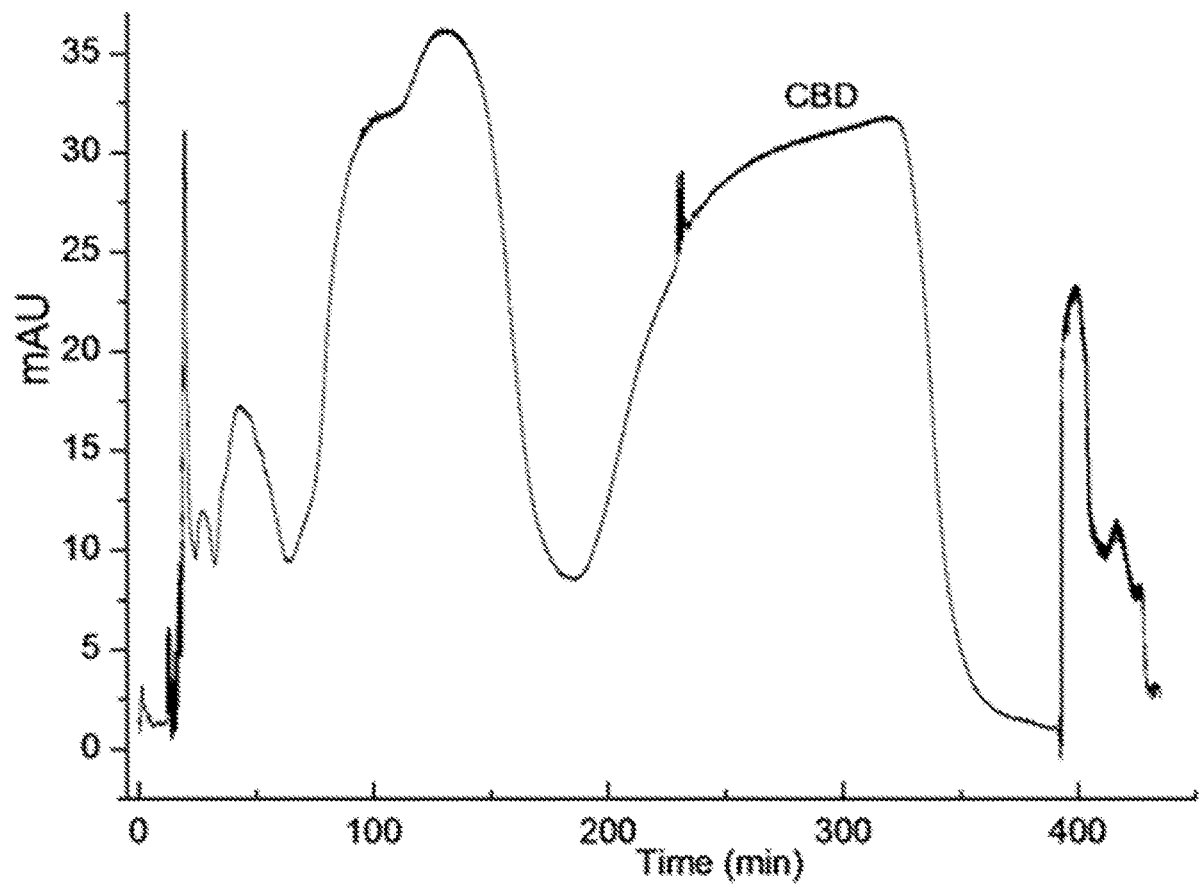
FIG. 3 is a graph showing the separation and purification of the crude extract of cannabidiol using a high-speed countercurrent chromatograph in Example 1.

(3) N-hexane, ethyl acetate, methanol and water were placed in a separatory funnel at a volume ratio of 5:0.5:5:1, shaked well, and left to rest for 20 min to separate the upper and lower phases, followed by ultrasonic degassing for 20 min. The upper phase served as a stationary phase and the lower phase served as a mobile phase. After preheating of the high-speed countercurrent chromatograph was initiated for 30 min, the recirculating water bath was set to 25° C., and the stationary phase was pumped into the chromatograph at a flow rate of 30 mL/min, followed by forward connection and forward rotation to start up the chromatograph so that the main engine reached a rotational speed of 800 r/min. After the rotational speed was stable, the mobile phase was pumped at a flow rate of 5 mL/min. After the two phases reached equilibrium in the pipeline, 1000 mg of the crude extract of cannabidiol was dissolved in 20 mL of the mobile phase, followed by sample injection and detection with a UV detector. The target peak component was collected and concentrated under reduced pressure to remove the organic phase. The precipitate precipitated during the decompression process was suction filtered and freeze-dried to obtain a cannabidiol monomer with a purity of 99.12% and no THC was detected, as illustrated in FIGS. 2 and 3.

EXAMPLE 2

(1) 10 kg industrial hemp was ground and dried, and added into an 80% aqueous ethanol solution at the material to liquid ratio of 1:10 (w/v, g/mL) to be mixed thoroughly and ultrasonically extracted for 100 min (control the temperature to below 45° C., and keep away from light). After ultrasonication, vacuum filtration was carried out, and the resulting filter residue was extracted repetitively for twice under the same conditions. The filtrate was combined, with the ethanol removed by vacuum rotary evaporation at 45° C., and then concentrated to have a relative density of 1.2, and 5-7 times of purified water was added. Under the condition of 5-8° C., it was subjected to water precipitation for 24 h, and filtered. The precipitate was dried under reduced pressure to obtain a crude hemp extract.

(2) The D101 macroporous resin was soaked in ethanol for 24 h, and then loaded into the chromatography column. It was washed with ethanol until the eluent in combination with the same volume of deionized water became a transparent solution. Then, it was washed with deionized water until the effluent was neutral; the crude hemp extract was dissolved in ethanol, and then injected into the D101 macroporous resin until the adsorption volume reached ⅔ of the total volume of the resin. The resin was first rinsed with deionized water at a flow rate of 2.5 BV/h, then rinsed with 10%, 30%, 70% and 80% aqueous ethanol solution respectively at a flow rate of 2.5 BV/h, and 70-80% elution fractions were collected. The ethanol was removed by vacuum rotary evaporation at 45° C. to obtain a crude extract of cannabidiol.

(3) N-hexane, methanol and water were placed in a separatory funnel at a volume ratio of 5:5:2.5, shaked well, and left to rest for 20 min to separate the upper and lower phases, followed by ultrasonic degassing for 20 min. The lower phase served as a stationary phase and the upper phase served as a mobile phase. After preheating of the high-speed countercurrent chromatograph was initiated for 30 min, the recirculating water bath was set to 25° C., and the stationary phase was pumped into the chromatograph at a flow rate of 30 mL/min, followed by forward connection and backward rotation to start up the chromatograph so that the main engine reached a rotational speed of 850 r/min. After the rotational speed was stable, the mobile phase was pumped at a flow rate of 10 mL/min. After the two phases reached equilibrium in the pipeline, 1000 mg of the crude extract of cannabidiol was dissolved in 20 mL of the mobile phase, followed by sample injection and detection with a UV detector. The target peak component was collected and concentrated under reduced pressure to remove the organic phase. The precipitate precipitated during the decompression process was suction filtered and freeze-dried to obtain a cannabidiol monomer with a purity of 99.75% and no THC was detected.

EXAMPLE 3

(1) 10 kg industrial hemp was ground and dried, and added into 80% aqueous ethanol solution at the material to liquid ratio of 1:8 (w/v, g/mL) to be mixed thoroughly and ultrasonically extracted for 120 min (control the temperature to below 45° C., and keep away from light). After ultrasonication, vacuum filtration was carried out, and the resulting filter residue was extracted repetitively for twice under the same conditions. The filtrate was combined, with the ethanol removed by vacuum rotary evaporation at 45° C., and then concentrated to have a relative density of 1.2, and 5-7 times of purified water was added. Under the condition of 5-8° C., it was subjected to water precipitation for 24 h, and filtered. The precipitate was dried under reduced pressure to obtain a crude hemp extract.

(2) The AB-8 macroporous resin was soaked in ethanol for 24 h, and then loaded into the chromatography column. It was washed with ethanol until the eluent in combination with the same volume of deionized water became a transparent solution. Then, it was washed with deionized water until the effluent was neutral; the crude hemp extract was dissolved in ethanol, and then injected into the AB-8 macroporous resin until the adsorption volume reached ⅔ of the total volume of the resin. The resin was first rinsed with deionized water at a flow rate of 2 BV/h, then rinsed with 10%, 30%, 50% and 80% aqueous ethanol solution respectively at a flow rate of 2 BV/h, and 80% elution fractions were collected. The ethanol was removed by vacuum rotary evaporation at 45° C. to obtain a crude extract of cannabidiol.

(3) N-hexane, methanol and water were placed in a separatory funnel at a volume ratio of 5:5:1, shaked well, and left to rest for 20 min to separate the upper and lower phases, followed by ultrasonic degassing for 20 min. The upper phase served as a stationary phase and the lower phase served as a mobile phase. After preheating of the high-speed countercurrent chromatograph was initiated for 30 min, the recirculating water bath was set to 25° C., and the stationary phase was pumped into the chromatograph at a flow rate of 30 mL/min, followed by forward connection and forward rotation to start up the chromatograph so that the main engine reached a rotational speed of 800 r/min. After the rotational speed was stable, the mobile phase was pumped at a flow rate of 5 mL/min. After the two phases reached equilibrium in the pipeline, 2000 mg of the crude extract of cannabidiol was dissolved in 20 mL of the mobile phase, followed by sample injection and detection with a UV detector. The target peak component was collected and concentrated under reduced pressure to remove the organic phase. The precipitate precipitated during the decompression process was suction filtered and freeze-dried to obtain a cannabidiol monomer with a purity of 99.50% and no THC was detected.

What is claimed is:

1. A method for preparing cannabidiol by separation and purification using high-speed countercurrent chromatography, comprising:
   step 1, subjecting industrial hemp flowers or leaves as raw materials to alcohol extraction and concentration, water precipitation, and vacuum rotary evaporation to obtain a crude hemp extract;
   step 2, dissolving the crude hemp extract in ethanol, then injecting it into a macroporous resin, followed by gradient elution to collect an elution section rich in cannabidiol and vacuum rotary evaporation to obtain a crude extract of cannabidiol; and
   step 3, performing separation and purification using high-speed countercurrent chromatography with n-hexane-ethyl acetate-methanol-water as a separation solvent system to collect cannabidiol fractions, recover the solvent, followed by post-treatment to obtain cannabidiol.

2. The method for preparing cannabidiol by separation and purification using high-speed countercurrent chromatography according to claim 1, wherein the alcohol extraction and concentration in the step 1 employs an ethanol solution with a concentration of 50~90% by volume, and the mass-volume ratio of the industrial hemp flowers or leaves to the ethanol solution is 1 g: (5~10) mL.

3. The method for preparing cannabidiol by separation and purification using high-speed countercurrent chromatography according to claim 1, wherein the water precipitation is performed at a temperature of 5~8° C. for 24 h.

4. The method for preparing cannabidiol by separation and purification using high-speed countercurrent chromatography according to claim 1, wherein the macroporous resin in the step 2 is D101 macroporous resin, AB-8 macroporous resin or HPD-100 macroporous resin.

5. The method for preparing cannabidiol by separation and purification using high-speed countercurrent chromatography according to claim 1, wherein the gradient elution in the step 2 employs an ethanol solution with a concentration of 5~85% by volume; and the elution section of the ethanol solution with a concentration of 70~85% by volume is collected.

6. The method for preparing cannabidiol by separation and purification using high-speed countercurrent chromatography according to claim 1, wherein the n-hexane-ethyl acetate-methanol-water in the step 3 has a volume ratio of 5:(0~1):5:(1~3).

7. The method for preparing cannabidiol by separation and purification using high-speed countercurrent chromatography according to claim 1, wherein the separation and purification using high-speed countercurrent chromatography in the step 3 specifically comprises: taking one phase in the separation solvent system as a stationary phase and another phase as a mobile phase; pumping the stationary phase at a flow rate of 30~50 mL/min into a high-speed countercurrent chromatograph, and pumping the mobile phase at a flow rate of 5~10 mL/min under the condition of 25~35° C. and a rotational speed of the main engine being 700~1000 r/min; after the two phases reach equilibrium, dissolving the crude extract of cannabidiol with the mobile phase, collecting cannabidiol fractions after detecting with a detector.

8. The method for preparing cannabidiol by separation and purification using high-speed countercurrent chromatography according to claim 7, wherein the crude extract of cannabidiol after being dissolved with the mobile phase has a concentration of 50~100 mg/mL, and the injection volume is 20 mL; and the detection wavelength is 220 nm.

9. The method for preparing cannabidiol by separation and purification using high-speed countercurrent chromatography according to claim 1, wherein the post-treatment in the step 3 includes concentration under reduced pressure, crystallization, and vacuum freeze-drying.

* * * * *